United States Patent [19]

Sato et al.

[11] 4,284,818

[45] Aug. 18, 1981

[54] PROCESS FOR PREPARING HEXAMETHYLTETRAHYDRONAPHTHALENES

[75] Inventors: Hiroshi Sato; Koiti Fujisawa, both of Toyonaka; Hideto Tojima, Kyoto; Seimei Yasui, Takarazuka, all of Japan

[73] Assignee: Sumitomo Chemical Company, Limited, Osaka, Japan

[21] Appl. No.: 19,587

[22] Filed: Mar. 12, 1979

[30] Foreign Application Priority Data

Mar. 30, 1978 [JP] Japan .................................. 53/37602

[51] Int. Cl.$^3$ .......................... C07C 2/68; C07C 45/46
[52] U.S. Cl. ..................... 568/323; 585/411; 585/323
[58] Field of Search ................ 260/586 C; 585/410, 585/323, 411; 568/322, 327, 323

[56] References Cited

U.S. PATENT DOCUMENTS

| 2,759,022 | 8/1956 | Fuchs | 585/323 |
| 2,851,501 | 9/1958 | Benz et al. | 585/410 |
| 3,278,621 | 10/1966 | Stofberg et al. | 568/312 |
| 3,379,782 | 4/1968 | Kahn | 585/411 |
| 3,856,875 | 12/1974 | Wood et al. | 585/410 |

FOREIGN PATENT DOCUMENTS 987747 2/1965 United Kingdom.
1442954 7/1976 United Kingdom.

OTHER PUBLICATIONS

Wood, T. F. et al., "Polycyclic Musks": J. Org. Chem., vol. 28, pp. 2248–2255 (1963).
Kirk–Othmer, "Encyclopedia of Chemical Technology", vol. 1, pp. 218 and 888, 2nd Ed. (1963).

Primary Examiner—Natalie Trousof
Assistant Examiner—L. Hendriksen
Attorney, Agent, or Firm—Stevens, Davis, Miller & Mosher

[57] ABSTRACT

1,1,3,4,4,6-Hexamethyl-1,2,3,4-tetrahydronaphthalene (HMT), which is an intermediate for the production of acetyl HMT valuable in the art of perfumery because of its musk-like odor properties, is produced with industrial advantages by reacting p-cymene with 2,3-dimethylbutene using a catalytic amount of an anhydrous aluminum halide in the presence of at least one member selected from secondary alkyl halides, tertiary alkyl halides, propargyl halides and allyl halides; and 7-acetyl HMT is obtained by acetylation of the above-obtained HMT.

18 Claims, No Drawings

PROCESS FOR PREPARING HEXAMETHYLTETRAHYDRONAPHTHALENES

The present invention relates to a process for producing 1,1,3,4,4,6-hexamethyl-1,2,3,4-tetrahydronaphthalene generally called 1,1,3,4,4,6-hexamethyltetralin (hereinafter referred to as "HMT" for brevity).

By acetylation of HMT, HMT can be converted to 7-acetyl-1,1,3,4,4,6-hexamethyl-1,2,3,4-tetrahydronaphthalene, which is well known as a musk perfume of tetralin series. This tetralin series musk is highly appreciated, particularly because of its high quality and long retention of odor, as a synthetic musk perfume substituting for the expensive, natural musk perfumes of macrocyclic ketone series. Consequently, various synthetic methods have been proposed. In these methods, HMT, a precursor of 7-acetyl-1,1,3,4,4,6-hexamethyl1,2,3,4-tetrahydronapthalene, is mainly synthesized by reaction between an A-group monomer including p-cymene, α,p-dimethylstyrene, dimethyl-p-tolycarbinol and 2-chloro-2-(p-tolyl)-propane, and a B-group monomer including 2,3-dimethylbutenes, dimethyl-isopropylcarbinol, neohexene and methyl-tert-butylcarbinol. As for this type of reaction, a common route may be assumed from the standpoint of reaction mechanism. In short, the reaction may be assumed to take the following route: Generation of p-cymylcarbonium ions from the A-group monomer and attack of the ions against the olefin or alcohol belonging to the B-group monomer, followed by the progress of cyclization and alkylation to form the HMT. It is not however clear whether or not this assumption holds in every case of the reaction.

On detailed investigation about the presently well-known synthetic methods, every method has the following drawbacks and may not be said to be complete from the technical and economical points of view. According to U.S. Pat. No. 2,759,022, a substance having a musk-like odor is obtained by reacting p-cymene with methyl-tert-butylcarbinol in the presence of sulfuric acid catalyst, followed by separation and then acetylation of the resulting product. But, there are no descriptions on the chemical structure and yield of the product. According to U.S. Pat. No. 2,851,501, a substance having a musk-like odor is obtained by reacting α,p-dimethylstyrene with 2,3-dimethylbutenes in acetic acid in the presence of sulfuric acid catalyst, followed by acetylation of the resulting product. But the patent says that this substance has an indane structure. U.S. Pat. No. 3,278,621 discloses that HMT is obtained by reacting α,p-dimethylstyrene with dimethyl-isopropylcarbinol or methyl-tert-butylcarbinol using sulfuric acid/acetic acid as catalyst, but there is no description on the yield. In the foregoing three methods, concentrated sulfuric acid is used in a large excess so that equipment is corroded and after-treatment becomes troublesome. According to U.S. Pat. No. 3,379,782 and Dutch Pat. No. 6,612,053, HMT is obtained by reacting α,p-dimethylstyrene with 2,3-dimethylbutenes using active clay or ion-exchange resin as catalyst. But, this method requires the recovery and re-use of the unreacted olefin because of a low conversion per one pass, and besides it is disadvantageous economically because α,p-dimethylstyrene is scarcely available and expensive. British Pat. No. 987,747 discloses that HMT is obtained by reacting 2-chloro-2-(p-tolyl)-propane with neohexene in the presence of a FriedelCrafts catalyst, and British Pat. No. 1,442,954 discloses that HMT is obtained by reacting p-cymene, neohexene and tert-alkyl halide in the presence of aluminum halide catalyst. These two methods are also not desirable for the following reasons: Firstly, neohexene, an olefin, used as a starting material, is scarcely available; secondly, on detailed investigation about the substantially preferred reaction conditions of the methods, it was found that halogen-containing compounds such as monochlorobenzene and ethylene dichloride, which are not too desirable in terms of safety, should be used as solvent, and that low reaction temperatures, substantially less than room temperature and preferably −10° to 10° C., are required so that the problem of process engineering, for example cooling, should be taken into account.

Previously, the inventors found a method for producing 2,3-dimethylbutenes, which are useful starting materials for the production of agricultural chemicals and fine chemicals, by the dimerization of propylene cheaply derived from petroleum. During the subsequent extensive study on the useful application of said 2,3-dimethylbutenes, the inventors found that HMT can be produced economically by reacting said cheap 2,3-dimethylbutenes with p-cymene in terms of availability of raw materials and cost, and studied a production process of HMT free from the foregoing drawbacks of the prior art. As a result, it was found that HMT can be obtained in a high yield by reacting 2,3-dimethylbutenes with p-cymene using anhydrous aluminum halide as catalyst in the presence of an active organohalogen compound. The inventors further investigated the present process for the production of HMT, and found that in carrying out the process of the present invention, halogen-containing solvents such as monochlorobenzene may be used, but paraffin solvents such as cyclohexane and n-hexane are rather preferred from the viewpoint of safty and process engineering, i.e. the yield is high and good results are obtained in the vicinity of room temperature. The present invention provides a process for producing 1,1,3,4,4,6-hexamethyl-1,2,3,4-tetrahydronaphthalene, which comprises reaction between p-cymene and a 2,3-dimethylbutene using a catalytic amount of anhydrous aluminum halide of the formula,

wherein $X_1$, $X_2$ and $X_3$ are the same or different, and are halogen atoms, provided that when two of $X_1$, $X_2$ and $X_3$ are fluorine atoms, another is a different halogen atom, in the presence of one member selected from the following organohalogen compounds of the formulae (I) to (IV); secondary alkyl halides of formula (I),

wherein $R^1$ and $R^2$ are each an alkyl group or may form a cyclic ring, and X is a halogen atom; tertiary alkyl halides of formula (II),

wherein $R^1$, $R^2$ and $R^3$ are each an alkyl group or two of them may form a cyclic ring, and X is a halogen atom; propargyl halides of formula (III),

  (III)

wherein R is a hydrogen atom or an alkyl group, and X is a halogen atom; and allyl halides of formula (IV),

  (IV)

wherein R is a hydrogen atom or an alkyl group and X is a halogen atom.

Anhydrous aluminum halides used as a catalyst in the present invention include aluminum chloride, aluminum bromide and aluminum iodide. In addition, there can be used other anhydrous aluminum halides having an optionally controlled acidity and association degree, such as monofluorodichloroaluminum, monobromodichloroaluminum and monoiododichloroaluminum. In the present invention, however, anhydrous aluminum chloride and anhydrous aluminum bromide give the best results. As 2,3-dimethylbutenes used as a material, both 2,3-dimethyl-1-butene and 2,3-dimethyl-2-butene can be used. But, 2,3-dimethyl-1-butene gives better results.

The compounds of the formula (I) include isopropyl chloride, sec-butyl chloride, sec-amyl chloride, cyclohexyl chloride and their homologues having halogen atoms other than a chlorine atom (i.e. fluorine, bromine, iodine). Compounds of formula (II) include tert-butyl chloride, tert-amyl chloride, 2-methyl-2-chloropentane, 3-methyl-3-chloropentane and their homologues having halogen atoms other than a chlorine atom (i.e. fluorine, bromine, iodine). Compounds of formula (III) include propargyl chloride, 1-chloro-2-butyne, 1-chloro-2-pentyne and their homologues having halogen atoms other than a chlorine atom (i.e. fluorine, bromine, iodine). Compounds of formula (IV) include allyl chloride, 1-chloro-2-butene, 1-chloro-3-methyl-2-butene, 1-chloro-2-pentene, 1-chloro-2-hexene and their homologues having halogen atoms other than a chlorine atom (i.e. fluorine, bromine, iodine). Of these active organo-halogen compounds (I) to (IV), tertiary alkyl halides such as tert-butyl chloride, tert-amyl chloride, 2-methyl-2-chloropentane and 3-methyl-3-chloropentane are particularly preferred.

These active organo-halogen compounds are used in an amount of 0.05 to 5.0 moles per mole of the 2,3-dimethylbutene. The preferred is 0.5 to 2.0 moles per mole of the 2,3-dimethylbutene. p-Cymene is used in an equimolar amount or more to the 2,3-dimethylbutene. From the economical point of view, however, a preferred range is from 1.5 to 4 moles per mole of the 2,3-dimethylbutene.

This reaction is generally carried out using a solvent, but it may be carried out without a solvent using p-cymene, one of the starting materials, in a large excess. Solvent include aliphatic hydrocarbons (e.g. n-hexane, n-heptane, n-octane, cyclohexane), halogenated aromatic hydrocarbons (e.g. monochlorobenzene, o-dichlorobenzene, bromobenzene, fluorobenzene) and halogenated aliphatic hydrocarbons (e.g. methylene chloride, chloroform, carbon tetrachloride, ethylene chloride, ethylidene chloride, 1,1,1-trichloroethane, 1,1,2-trichloroethane, 1,1,2,2-tetrachloroethane, 1,2-dichloroethylene, trichloroethylene, tetrachloroethylene, 1,2,3-trichloropropane, amyl chloride, ethylene bromide). Of these solvents, aliphatic hydrocarbons are particularly preferred in terms of the yield of HMT, safety and process engineering.

The reaction temperature is generally within a range of $-30°$ to $50°$ C. The optimum reaction temperature varies somewhat depending upon the solvent, and when aliphatic hydrocarbons such as cyclohexane are used as a solvent, it is preferably within a range of $-10°$ to $40°$ C., more preferably $10°$ to $30°$ C. When halogenated aliphatic or halogenated aromatic hydrocarbons are used as a solvent, the reaction temperature is favorably $-20°$ to $10°$ C.

The anhydrous aluminum halide, a catalyst, is generally used within a range of 1 to 20% by mole based on 2,3-dimethylbutenes.

1,1,3,4,4,6-Hexamethyl-1,2,3,4-tetrahydronaphthalene (HMT) obtained by the process of the present invention can be acetylated by the usual methods, giving 7-acetyl-1,1,3,4,4,6-hexamethyl-1,2,3,4-tetralin which is well known as a musk perfume of tetralin series.

The present invention will be illustrated specifically with reference to the following examples, which are not however to be interpreted as limiting the invention thereto.

EXAMPLE 1

Atmosphere in a 500-ml round bottomed flask equipped with a dropping funnel, condenser and stirrer was replaced with nitrogen, and anhydrous aluminum chloride (2.0 g) and monochlorobenzene (40 ml) were added threto. Thereafter, a mixture comprising p-cymene (89 g), 2,3-dimethyl-1-butene (15 g) and tert-butyl chloride (18.5 g) was added dropwise at $-5°$ over 2 hours. Then, the reaction solution was poured into ice water to stop the reaction, and the oily layer was washed with 5% aqueous sodium hydroxide solution and then water and dried over sodium sulfate.

The oily layer thus treated was distilled at atmospheric pressure to remove the solvent and unreacted p-cymene, and then vacuum-distilled to obtain 18.5 g of a fraction having a boiling point of $104°$-$107°$ C./3.5 mmHg. By gas-chromatographic analysis, it was found that this fraction was 1,1,3,4,4,6-hexamethyl-1,2,3,4-tetrahydronaphthalene (HMT) having a purity of 94%. Melting point: $58°$ C. The yield of HMT was 45% based on 2,3-dimethyl-1-butene (as converted to 100% purity basis).

On recrystallizing this HMT fraction from isopropyl alcohol of the same amount, white and pure HMT having a melting point of $67°$ C. was obtained. Gas-chromatographic analysis showed that the purity of the HMT was 98%. The results of IR and NMR analyses of the HMT agreed with those of the authentic sample, 1,1,3,4,4,6-hexamethyl-1,2,3,4-tetrahydronaphthalene, synthesized separately.

Acetylation of the purified HMT was carried out as follows: Atmosphere in a 200-ml flask equipped with a condenser was replaced with nitrogen, and HMT (10 g), acetyl chloride (4 g) and dichloroethane (40 g) were added thereto; powdery anhydrous aluminum chloride (7.4 g) was added thereto in six portions with stirring by a Teflon-coated magnetic stirrer followed by reaction at $20°$ C. for 1.5 hours; then, the reaction solution was poured into ice water (50 g) to stop the reaction, and the oily layer was washed with 5% aqueous sodium hydroxide solution and then twice with water, followed by drying over sodium sulfate; the liquor thus obtained was distilled at atmospheric pressure to remove the solvent, dichloroethane, and vacuum-distilled to obtain 11 g of a fraction having a boiling point of 145°-152° C./2 mmHg (melting point 52° C.). On recrystallizing the fraction from ethanol of the same amount at 0° C., a white solid having a strong musk-like odor was obtained. Melting point: 56° C. Purity by gas-chromatography: 98%. The results of IR and NMR analyses of the product agreed with those of the authentic sample, 7-acetyl-1,1,3,4,4,6-hexamethyl-1,2,3,4-tetrahydronaphthalene, synthesized separately.

EXAMPLE 2

Experiment was carried out in completely the same manner as in Example 1 except that cyclohexane (40 ml) was used in place of monochlorobenzene. Thus, 23 g of a fraction having a boiling point of 104°-108° C./3.5 mmHg was obtained. Gas-chromatographic analysis showed that the fraction was HMT having a purity of 93%. Melting point: 57° C. The yield of HMT was 55.4% based on 2,3-dimethyl-1-butene (as converted to 100% purity basis).

EXAMPLE 3

Experiment was carried out in completely the same manner as in Example 1 except that the predetermined amounts of aluminum halides shown in Table 1 were used in place of aluminum chloride. The results are shown in Table 1.

TABLE 1

| No. | Aluminum halide Name | Amount (g) | Yield of HMT[1] (%) |
|---|---|---|---|
| 1 | Aluminum tribromide | 4.0 | 35.0 |
| 2 | Aluminum triiodide | 6.1 | 27.0 |
| 3 | Aluminum monofluorodichloride | 1.8 | 45.0 |
| 4 | Aluminum monobromodichloride | 2.7 | 40.5 |
| 5 | Aluminum monoiododichloride | 3.4 | 40.0 |

Note
[1] Yield based on 2,3-dimethyl-1-butene

EXAMPLE 4

Experiment was carried out in completely the same manner as in Example 2 except that the predetermined amounts of organo-halogen compounds shown in Table 2 were used in place of tert-butyl chloride. The results are shown in Table 2.

TABLE 2

| No. | Organo-halogen compound Name | Amount (g) | Yield of HMT[1] (%) |
|---|---|---|---|
| 1 | iso-Propyl chloride | 16.8 | 35.0 |
| 2 | Cyclohexyl chloride | 25.4 | 34.2 |
| 3 | tert-Butyl bromide | 29.3 | 52.3 |
| 4 | tert-Amyl chloride | 22.8 | 51.0 |
| 5 | Allyl chloride | 16.4 | 29.0 |
| 6 | Propargyl chloride | 16.0 | 28.5 |
| 7 | iso-Propyl bromide | 26.3 | 30.0 |

Note
[1] Yield based on 2,3-dimethyl-1-butene

EXAMPLE 5

Experiment was carried out in completely the same manner as in Example 1 except that 40 ml each of the solvents shown in Table 3 was used in place of chlorobenzene. The results are shown in Table 3. Experiment No. 5 was carried out without a solvent.

TABLE 3

| No. | Solvent | Yield of HMT[1] (%) |
|---|---|---|
| 1 | n-Heptane | 52.0 |
| 2 | Chloroform | 45.0 |
| 3 | o-Dichlorobenzene | 40.5 |
| 4 | Fluorobenzene | 42.0 |
| 5 | None | 38.0 |

Note
[1] Yield based on 2,3-dimethyl-1-butene

EXAMPLE 6

Atmosphere in a 100-ml round bottomed flask equipped with a dropping funnel, condenser and stirrer was replaced with nitrogen, and anhydrous aluminum chloride (1.33 g), cyclohexane (17.1 ml) and tert-butyl chloride (1.2 ml) were added thereto. Thereafter, a mixture of p-cymene (8.9 g) and 2,3-dimethyl-1-butene (11.1 g) was added dropwise thereto at 20° C. over 2 hours. Then, the reaction solution was treated in the same manner as in Example 1. The yield of HMT was 21.8% based on 2,3-dimethyl-1-butene.

EXAMPLE 7

Experiment was carried out in completely the same manner as in Example 6 except that the amount of p-cymene was increased from 8.9 g to 17.7 g. The yield of HMT was 30.2% based on 2,3-dimethyl-1-butene.

EXAMPLE 8

Atmosphere in a 2-liter separable flask equipped with a baffle and turbine propeller was replaced with nitrogen, and cyclohexane (212 g) and anhydrous aluminum chloride (20.0 g) were added thereto. Thereafter, a mixture comprising 2,3-dimethyl-1-butene (84 g), p-cymene (268 g) and tert-butyl chloride (104.5 g) was added dropwise thereto from the dropping funnel at 20° C. over 3 hours with vigorous stirring. After the addition was finished, the reaction solution was immediately poured into ice water (700 g) to stop the reaction and treated in the same manner as in Example 1 to obtain 134 g of HMT. The yield of HMT was 62% based on 2,3-dimethyl-1-butene. Purity: 96%.

What is claimed is:
1. A process for producing 1,1,3,4,4,6-hexamethyl-1,2,3,4-tetrahydronaphthalene, which comprises reaction between p-cymene and a 2,3-dimethylbutene in an aliphatic hydrocarbon or cyclohexane solvent using a catalytic amount of anhydrous aluminum halide of the formula,

$$AlX_1X_2X_3$$

wherein $X_1$, $X_2$ and $X_3$ are the same or different, and are halogen atoms, provided that $X_1$, $X_2$ and $X_3$ may not be all fluorine atoms, in the presence of secondary alkyl halides of formula (I),

wherein R¹ and R² are each an alkyl group or may form a cyclic ring, and X is a halogen atom; tertiary alkyl halides of formula (II),

wherein R¹, R² and R³ are each an alkyl group or two of them may form a cyclic ring, and X is a halogen atom; propargyl halides of formula (III), $$RC\equiv C-CH_2-X \quad (III)$$

wherein R is a hydrogen atom or an alkyl group, and X is a halogen atom; or allyl halides of formula (IV), $$R-CH=CH-CH_2-X \quad (IV)$$

wherein R is a hydrogen atom or an alkyl group and X is a halogen atom.

2. A process according to claim 1, wherein the 2,3-dimethylbutene is 2,3-dimethyl-1-butene.

3. A process according to claim 1, wherein the 2,3-dimethylbutene is 2,3-dimethyl-2-butene.

4. A process according to claim 1, wherein the organo-halogen compound of formula (I), (II), (III) or (IV) is used in an amount of 0.05 to 5.0 moles per mole of the 2,3-dimethylbutene.

5. A process according to claim 1, wherein the organo-halogen compound of formula (I), (II), (III) or (IV) is used in an amount of 0.5 to 2.0 moles per mole of the 2,3-dimethylbutene.

6. A process according to claim 1, wherein the secondary alkyl halide of formula (I) is isopropyl chloride, sec-butyl chloride, sec-amyl chloride, cyclohexyl chloride, or their homologues having a halogen atom other than chlorine.

7. A process according to claim 1, wherein the tertiary alkyl halide of formula (II) is tert-butyl chloride, tert-amyl chloride, 2-methyl-2-chloropentane, 3-methyl-3-chloropentane or their homologues having a halogen atom other than chlorine.

8. A process according to claim 1, wherein the propargyl halide of formula (III) is propargyl chloride, 1-chloro-2-butyne, 1-chloro-2-pentyne and their homologues having a halogen atom other than chlorine.

9. A process according to claim 1, wherein the allyl halide of formula (IV) is allyl chloride, 1-chloro-2-butene, 1-chloro-3-methyl-2-butene, 1-chloro-2-pentene, 1-chloro-2-hexene or their homologues having a halogen atom other than chlorine.

10. A process according to claim 1, wherein p-cymene is used in an equimolar amount or more to the 2,3-dimethylbutene.

11. A process according to claim 1, wherein p-cymene is used in an amount of 1.5 to 4 moles per mole of the 2,3-dimethylbutene.

12. A process according to claim 1, wherein the hydrocarbon solvent is n-hexane, n-heptane, n-octane or cyclohexane.

13. A process according to claim 1, wherein the reaction is effected at a temperature of −30° to 50° C.

14. A process according to claim 1, wherein the aluminum halide is aluminum chloride, aluminum bromide, monofluorodichloroaluminum, monobromodichloroaluminum or monoiododichloroaluminum.

15. A process according to claim 1, wherein the aluminum halide is used within a range of 1 to 20% by mole based on the 2,3-dimethylbutene.

16. A process for producing 7-acetyl-1,1,3,4,4,6-hexamethyltetrahydronaphthalene, which comprises acetylation of 1,1,3,4,4,6-hexamethyltetrahydronaphthalene obtained according to claim 1.

17. 1,1,3,4,4,6-Hexamethyltetrahydronaphthalene obtained according to claim 1.

18. A process according to claim 1, wherein the reaction is effected at a temperature of 10° to 30° C.

* * * * *